United States Patent [19]

Lang et al.

[11] Patent Number: 4,867,751
[45] Date of Patent: Sep. 19, 1989

[54] USE OF BENZOQUINONES FOR THE DIRECT DYEING OF KERATIN FIBRES

[75] Inventors: Gérard Lang, Saint-Gratien; Alain Malaval, Aulnay-sous-Bois; Jean-Francois Grollier, Paris; Georges Rosenbaum, Asnieres, all of France

[73] Assignee: L'Oreal, Paris, France

[21] Appl. No.: 682,475

[22] Filed: Dec. 17, 1984

Related U.S. Application Data

[63] Continuation of Ser. No. 445,967, Dec. 1, 1982, abandoned.

[30] Foreign Application Priority Data

Dec. 2, 1981 [LU] Luxembourg ............................ 83807

[51] Int. Cl.$^4$ ................................................ A61K 7/13
[52] U.S. Cl. ........................................... 8/405; 8/428
[58] Field of Search .................................... 8/405, 428

[56] References Cited

U.S. PATENT DOCUMENTS

| | | | |
|---|---|---|---|
| 1,691,500 | 11/1928 | Shaw ........................................ | 8/662 |
| 2,086,337 | 7/1937 | Schirm ...................................... | 8/662 |
| 2,183,997 | 12/1939 | McNally et al. ......................... | 8/662 |
| 2,695,259 | 11/1954 | Charie ...................................... | 8/433 |
| 2,745,788 | 5/1956 | Frohnsdorff et al. ................... | 8/429 |
| 3,041,244 | 6/1962 | Feit et al. ................................ | 8/408 |
| 3,919,265 | 11/1975 | Bugaut et al. ........................... | 8/416 |
| 3,981,676 | 9/1976 | Ghilardi et al. ......................... | 8/406 |
| 4,023,926 | 5/1977 | Bugaut et al. ........................... | 8/431 |
| 4,104,021 | 8/1978 | Lapidus et al. ......................... | 8/429 |
| 4,358,286 | 11/1982 | Grollier et al. ......................... | 8/429 |

FOREIGN PATENT DOCUMENTS 277833 9/1927 United Kingdom ................... 8/662

OTHER PUBLICATIONS

"Chemical Abstracts", vol. 85 (1976), 68133f.
"Chemical Abstracts", vol. 85 (1976), 68134.

*Primary Examiner*—Douglas W. Robinson
*Attorney, Agent, or Firm*—Fleit, Jacobson, Cohn, Price Holman & Stern

[57] ABSTRACT

The invention relates to the use, for dyeing keratin fibres, and in particular human hair, of benzoquinone derivatives of the formula:

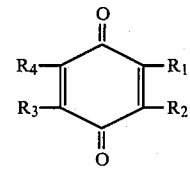

in which $R_1$ and $R_3$ independently of one another denote hydrogen, a hydroxyl group, an alkoxy group or an optionally hydroxylated alkyl group, and $R_2$ and $R_4$ independently of one another denote hydrogen, hydroxyl, alkoxy, alkyl, or phenyl optionally substituted by OH, these compounds having at most two alkyl or alkoxy groups on the quinone ring; if one of the radicals $R_1$, $R_2$, $R_3$ or $R_4$ denotes a methyl, hydroxyl or methoxy group, at least one of the other substituents is different from hydrogen, and if two of these substituents $R_1$, $R_2$, $R_3$ or $R_4$ are identical and located in the para-position relative to one another and denote hydroxyl or methoxy, at least one of the other two substituents is different from hydrogen.

14 Claims, No Drawings

USE OF BENZOQUINONES FOR THE DIRECT DYEING OF KERATIN FIBRES

This application is a continuation of application Ser. No. 445,967, filed Dec. 1, 1982, now abandoned.

The present invention relates to the use of benzoquinone derivatives for the direct dyeing of keratin fibres, and in particular human hair.

The dyeing of keratin fibres, such as human hair, feathers and animal hair, has been carried out using dyestuffs such as oxidation dyestuffs, which develop their coloration during an oxidative process in the presence of an oxidising agent, such as hydrogen peroxide, and direct dyestuffs, which are capable of dyeing the keratin fibres by themselves, and more particularly nitro derivatives of the benzene series, aminoanthraquinone dyestuffs, xanthene dyestuffs, azine dyestuffs, azo dyestuffs and indoamine dyestuffs.

We have discovered that a particular class of benzoquinones makes it possible to dye human hair directly, even at ambient temperature. These compounds, which have never been used for the direct dyeing of keratin fibres, and in particular for dyeing human hair, lead to very strong shades in a very wide range of colours, and make it possible to produce both blue shades and orange or red shades. These dyeings have an excellent fastness to washing and a good stability to light.

These dyestuffs have a good affinity, making them particularly suitable for dyeing human hair.

The present invention thus relates to the use of these benzoquinone derivatives for dyeing keratin fibres, and in particular human hair.

The benzoquinone derivatives used according to the invention correspond to the general formula:

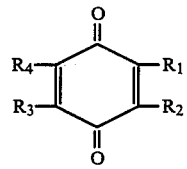

in which $R_1$ and $R_3$ independently of one another denote hydrogen, a hydroxyl group, an alkoxy group or an optionally hydroxylated alkyl group, and $R_2$ and $R_4$ independently of one another denote hydrogen, hydroxyl, alkoxy, alkyl or phenyl optionally substituted by OH, these compounds having at most two alkyl or alkoxy groups on the quinone ring; if one of the radicals $R_1$, $R_2$, $R_3$ or $R_4$ denotes a methyl, hydroxyl or methoxy group, at least one of the other substituents is different from hydrogen, and if two of these substituents $R_1$, $R_2$, $R_3$ or $R_4$ are identical and located in the para-position relative to one another and denote hydroxyl or methoxy, at least one of the other two substituents is different from hydrogen.

In the abovementioned formula, the alkyl and alkoxy groups preferably denote groups having from 1 to 3 carbon atoms.

Typically $R_1$ and/or $R_3$ denotes a hydrogen atom or a hydroxyl, methyl, iso-propyl, ethyl, hydroxymethyl or methoxy group and $R_2$ and/or $R_4$ denotes a hydrogen atom or a hydroxyl, methyl, iso-propyl, hydroxymethyl, methoxy, phenyl, 3- or 4-hydroxyphenyl or 3,4-dihydroxyphenyl group.

The dyestuffs which are more particularly preferred for use in the present invention include the following: 1,4-benzoquinone, 2,3,5,6-tetrahydroxy-1,4-benzoquinone, 2-hydroxy-3-methyl-6-methoxy-1,4-benzoquinone, 2,5-dihydroxy-3-methyl-6-methoxy-1,4-benzoquinone, 2,5-dihydroxy-3,6-dimethoxy-1,4-benzoquinone, 2-hydroxy-3-methyl-5,6-dimethoxy-1,4-benzoquinone, 2,5-dihydroxy-3-methyl-1,4-benzoquinone and 2-hydroxy-3-methoxy-5,6-dimethyl-1,4-benzoquinone.

Other dyestuffs which are particularly valuable are the following: 2-hydroxy-6-methyl-1,4-benzoquinone, 2-hydroxy-3-methoxy-6-methyl-1,4-benzoquinone, 2,3-dihydroxy-5-methyl-1,4-benzoquinone, 2,3-dihydroxy-5,6-dimethyl-1,4-benzoquinone, 2,6-dimethyl-1,4-benzoquinone, 2-methyl-5-isopropyl-1,4-benzoquinone, 2,5-dihydroxy-3,6-diphenyl-1,4-benzoquinone, and 2,5-dihydroxy-3,6-di-(4'-hydroxyphenyl)-1,4-benzoquinone.

A large number of the benzoquinone derivatives used in the invention are dyestuffs derived from one or more natural animal or vegetable origins.

The following may be mentioned more particularly amongst the compounds of natural origin which are benzoquinone derivatives as defined above:

TABLE I

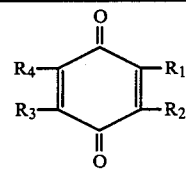

| COMMON NAME | SUBSTITUENTS | | | | ORIGIN |
|---|---|---|---|---|---|
| | $R_1$ | $R_2$ | $R_3$ | $R_4$ | |
| BENZOQUINONE | H | H | H | H | ARTHROPODA Spp. |
| GENTISYLQUINONE | $CH_2OH$ | H | H | H | *PENICILLIUM URTICAE* |
| — | $C_2H_5$ | H | H | H | ARTHROPODA Spp. |
| ORTHO-XYLO-QUINONE | $CH_3$ | $CH_3$ | H | H | " |
| PARA-XYLO-QUINONE | $CH_3$ | H | $CH_3$ | H | " |
| THYMOQUINONE | $CH_3$ | H | i-$C_3H_7$ | H | *SESELI HIPPOMARATHRUM* |
| — | $OCH_3$ | H | H | H | ARTHROPODA Spp. |
| COPRININE | $OCH_3$ | H | $CH_3$ | H | *LENTINUS DEGENER* |
| — | $OCH_3$ | $CH_3$ | H | H | ARTHROPODA Spp. |
| — | $OCH_3$ | H | H | $OCH_3$ | *TRITICIS VULGARE*, and the like |
| SPINULOSINE | OH | $OCH_3$ | OH | $CH_3$ | *PENICILLIUM SPINULOSUM* |

TABLE I-continued

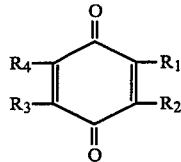

| COMMON NAME | SUBSTITUENTS | | | | ORIGIN |
|---|---|---|---|---|---|
| | $R_1$ | $R_2$ | $R_3$ | $R_4$ | |
| FUMIGATINE | OH | $OCH_3$ | H | $CH_3$ | *ASPERGILLUS FUMIGATUS* |
| — | OH | H | H | $CH_3$ | *ASPERGILLUS FUMIGATUS* |
| — | $OCH_3$ | OH | H | $CH_3$ | " |
| — | OH | OH | H | $CH_3$ | " |
| — | OH | H | OH | $CH_3$ | " |
| — | OH | $OCH_3$ | $CH_3$ | $CH_3$ | *GLIOCLAUDIUM ROSEUM* |
| — | OH | OH | $CH_3$ | $CH_3$ | " |
| AURANTIOGLIO-CLADINE | $OCH_3$ | $OCH_3$ | $CH_3$ | $CH_3$ | " |
| — | OH | H | OH | $C_2H_5$ | *ECHINOTRIX DIADEMA* |
| — | OH | $CH_3$ | H | $OCH_3$ | *LENTINUS DEGENER* |
| SHANORELLINE | OH | $CH_3$ | $CH_3$ | $CH_2OH$ | *SHANORELLA SPIROTRICHA* |
| POLYPORIC ACID | OH | phenyl | OH | phenyl | *POLYPORUS NIDULANS,* and the like |
| 3,6-DIHYDROXY-THYMOQUINONE | OH | $CH_3$ | OH | $i$-$C_3H_7$ | *JUNIPERUS CHINENSIS* |
| 3-HYDROXYTHYMO-QUINONE | OH | $CH_3$ | H | $i$-$C_3H_7$ | " |
| ATROMENTINE | OH | 4-OH—phenyl | OH | 4-OH—phenyl | *PAXILLUS ATROMENTOSUS* |
| LEUCOMELON | OH | 3,4-di-(OH)—phenyl | OH | 4-OH—phenyl | *POLYPORUS LEUCOMELAS* |
| VOLUCRISPORINE | H | 3-OH—phenyl | H | 3-OH—phenyl | *VOLUCRISPORA AURANTIACA* |

The dyestuffs according to the invention can be used either in the form of products obtained by synthesis, or in the form of isolated products, liquid or solid extracts, or homogenised masses of whole organisms or parts of organisms, these last forms being obtained from the natural sources.

These dyestuffs can be used by themselves or in a mixture in dyeing compositions for keratin fibres, in particular human hair.

The dyeing compositions for keratin fibres, and in particular for human hair, according to the present invention contain at least one dyestuff corresponding to the formula (I) defined above, in a cosmetically acceptable medium.

These compositions generally contain the dyestuffs of the formula (I) in concentrations of 0.01% to 5% by weight, but preferably 0.05 to 3% by weight, relative to the total weight of the dyeing composition.

The compositions for dyeing human hair, according to the invention, can be presented in a variety of forms, such as liquids, creams, gels, oils, powders or any other form suitable for dyeing the hair. They can also be packaged in aerosol flasks in the presence of a propellant.

They can contain other direct dyestuffs, such as anthraquinone dyestuffs described in British Specification No. 2 093 867, azo dyestuffs, nitro dyestuffs of the benzene series, indophenols, indamines, indoanilines and hydroxylated benzaldehyde derivatives.

Compositions which are more particularly preferred are those in which the benzoquinone derivatives are used in association with other quinone dyestuffs, such as the naphthoquinones described in our Application filed this same day under the title: Use of hydroxynaphthoquinones for dyeing human keratin fibres (Our N 35890; Luxembourg Application No. 83 806).

When used, these additional dyestuffs are suitably present in concentrations from 0.01 to 5% by weight and preferably from 0.1 to 3% by weight.

One of the particularly preferred embodiments of the compositions according to the invention is in the form of poultices. In this case, the quinone derivatives used in this invention, and preferably the quinone derivatives of natural origin, which can adopt the various forms mentioned above, can be prepared in the form of a powder which is stable on storage, and this is introduced into a solid medium which can be composed of powder, flour or a starchy or mucilagenous substance, which is diluted with an appropriate liquid at the time of use, so as to form a mixture having a consistency suitable for application to the hair.

The powders used in the poultices according to the invention can be insoluble substances, such as silicas, plants, clays, plants powdered after solvent extraction of their active principle, or alternatively plants or animals containing the natural benzoquinones defined above. The liquid used to dilute the powder can be water and/or a cosmetically acceptable solvent such as an alcohol, glycol or oil. The viscosity generally obtained after mixing is from 300 to 5,000 centipoises.

It is of course possible to introduce other dyestuffs of natural or synthetic origin into these compositions, in addition to the benzoquinone derivatives. Other natural dyestuffs which may be mentioned in this respect are lawsone, juglone, indigo and the plants or extracts containing these dyestuffs.

The cosmetically acceptable medium of the other embodiments of dyeing compositions for human hair, according to the invention, is generally aqueous and can contain anionic, cationic, non-ionic or amphoteric surface-active agents or a mixture thereof.

Amongst the preferred surface-active agents, there may be mentioned, more particularly, soaps, alkylbenzenesulphonates, alkylnaphthalenesulphonates, fatty alcohol sulphates, ether-sulphates or sulphonates, quaternary ammonium salts, fatty acid diethanolamides, and polyoxyethyleneated or polyglycerolated acids, alcohols or amides. These surface-active agents are suitably present in the compositions according to the invention in an amount of 0.1 to 55% by weight and preferably 1 to 40% by weight, relative to the total weight of the composition.

These compositions can also contain organic solvents, examples of which include lower alkanols, such as ethanol and isopropanol, polyols, such as glycerol, glycols or glycol esters, such as ethylene glycol monobutyl ether, ethylene glycol, propylene glycol, and diethylene glycol monoethyl ether and monomethyl ether. These solvents are preferably used in amounts from 1 to 60% by weight, more particularly from 3 to 30% by weight, relative to the total weight of the composition.

The compositions can also contain anionic, non-ionic, cationic or amphoteric polymers or a mixture thereof, suitably in an amount from 0.1 to 5% by weight.

The compositions according to the invention can be thickened, preferably with gums and mucilages, such as sodium alginate, gum arabic, guar gum and carbo gum, cellulose derivatives, such as methylcellulose, hydroxyethylcellulose, hydroxypropylcellulose and carboxymethylcellulose, and various polymers serving this purpose, in particular, acrylic acid derivatives. It is also possible to use inorganic thickeners, such as bentonite. These thickeners are preferably present in an amount from 0.1 to 5% by weight, in particular from 0.5 to 3% by weight, relative to the total weight of the composition.

Any other adjuvants normally used in hairdyeing compositions, such as penetrating agents, sequestering agents, buffers, perfumes and antioxidants, can of course be included in the compositions according to the invention.

The benzoquinone derivatives of the formula (I) can generally be employed in a pH range of 1 to 7. However, particularly advantageous results can be obtained for acid pH values and more particularly from pH 2 to 5, the range from 2 to 4.5 being particularly preferred.

The pH of the dyeing compositions of the invention can be adjusted with organic or mineral acids, alkali metal or alkaline earth metal hydroxides or carbonates, ammonia, or organic bases, such as alkanolamines, such as mono-, di- or tri-ethanolamine, or alkylamines. The preferred acids are hydrochloric acid, citric acid, tartaric acid, lactic acid and acetic acid.

The process of dyeing human keratin fibres, and in particular hair, according to the invention is essentially characterised in that at least one composition such as defined above is applied to the hair, generally before or after shampooing, it is left for, say, 5 to 60 minutes, and preferably 5 to 40 minutes, and the hair is rinsed and dried. A setting composition can also be applied to the hair after shampooing, and the hair is then dried.

The hair can also be dyed by multistep processes in which at least one step consists in applying a dyestuff of the formula (I). These multistep processes can use compositions having different pH values according to the nature of the dyestuffs present. Thus, for example, it may be possible to carry out multistep dyeing using, first, a composition containing the benzoquinone derivative and having an acid pH, preferably of 2 to 5, and then dyeing in a second step using a composition having an alkaline pH (7 to 12) and capable of containing dyestuffs which act in an alkaline medium or which are stable in this medium.

The Examples which follow further illustrate the present invention.

EXAMPLE 1

The following composition is prepared:

| | |
|---|---|
| 2,3,5,6-Tetrahydrobenzoquinone dihydrate | 0.3 g |
| Cetyl alcohol | 17.0 g |
| MERGITAL CS 15 E | 6.0 g |
| Oleyl alcohol | 3.0 g |
| Citric acid q.s. | pH 2.3 |
| Distilled water q.s. | 100 g |

This cream is applied to light chestnut hair. After a period of 30 minutes, the hair is rinsed, washed and dried. It then possesses an intense golden coppery sheen.

EXAMPLE 2

The following composition is prepared:

| | |
|---|---|
| 2,5-Dihydroxy-3-methyl-1,4-benzoquinone | 0.75 g |
| 2-Hydroxy-3-methoxy-5,6-dimethyl-1,4-benzoquinone | 0.2 g |
| Cetyl alcohol | 17.0 g |
| MERGITAL CS 15 E | 6.0 g |
| Oleyl alcohol | 3.0 g |
| Citric acid q.s. | pH 2 |
| Distilled water q.s. | 100 g |

This cream is applied to light chestnut hair for 30 minutes. After 30 minutes, the hair is rinsed. It is shampooed and dried. The hair then has an auburn sheen.

EXAMPLE 3

The following composition is prepared:

| | |
|---|---|
| 2,5-Dihydroxy-1,4-benzoquinone | 0.07 g |
| 2,3,5,6-Tetrahydroxy-1,4-benzoquinone dihydrate | 0.04 g |
| Vinyl acetate/crotonic acid copolymer (90/10) | 1.8 g |
| Vinylpyrrolidone/vinyl acetate copolymer (60/40) | 0.4 g |
| 96° strength ethyl alcohol q.s. | 50° alcoholic strength |
| Citric acid q.s. | pH 3 |
| Distilled water q.s. | 100 g |

This composition is applied to blond hair as a setting lotion. After drying, the hair is coloured a golden beige blond shade.

EXAMPLE 4

The following composition is prepared:

| | |
|---|---|
| 2,5-Dihydroxy-3-methyl-6-methoxy-1,4-benzoquinone | 0.8 g |
| 2-Hydroxy-1,4-naphthoquinone | 0.1 g |
| 2-Amino-3-hydroxy-nitrobenzene | 0.1 g |
| Cetyl alcohol | 17.0 g |
| MERGITAL CS 15 E | 6.0 g |
| Oleyl alcohol | 3.0 g |
| Acetic acid q.s | pH 2.2 |

| -continued | |
|---|---|
| Distilled water q.s. | 100 g |

This cream is applied to moderately sensitised, natural light chestnut hair. After a period of 30 minutes, the hair is rinsed. It is shampooed and dried. The hair then possesses a golden brown sheen.

EXAMPLE 5

The following composition is prepared:

| | |
|---|---|
| 2,5-Dihydroxy-3,6-dimethoxy-1,4-benzoquinone | 0.4 g |
| 2-Hydroxy-3-methyl-6-methoxy-1,4-benzoquinone | 0.45 g |
| 2,3-Dimethoxy-6-methyl-1,4-benzoquinone | 0.35 g |
| Cetyl alcohol | 17.0 g |
| MERGITAL CS 15 E | 3.0 g |
| Oleyl alcohol | 3.0 g |
| Citric acid q.s. | pH 2 |
| Distilled water q.s. | 100 g |

This cream is applied for 30 minutes to hair containing a very high percentage of white hair. After rinsing and shampooing, the dried hair is coloured a natural grey shade.

EXAMPLE 6

The following dyeing composition is prepared:

| | |
|---|---|
| 1,4-Benzoquinone | 0.6 g |
| Cetyl alcohol | 17.0 g |
| MERGITAL CS 15 E | 6.0 g |
| Oleyl alcohol | 3.0 g |
| Citric acid q.s. | pH 2.7 |
| Distilled water q.s. | 100 g |

This composition is applied in the form of a cream to freshly permed, natural light chestnut hair. After a period of 30 minutes, the hair is rinsed, washed and dried. It possesses an intense golden sheen.

EXAMPLE 7

The following composition is prepared:

| | |
|---|---|
| 2,5-Dihydroxy-1,4-benzoquinone | 0.4 g |
| 2,5-Dihydroxy-3-methyl-6-methoxy-1,4-benzoquinone | 0.5 g |
| Cetyl alcohol | 17.0 g |
| MERGITAL CS 15 E | 6.0 g |
| Oleyl alcohol | 3.0 g |
| Citric acid q.s. | pH 2 |
| Distilled water q.s. | 100 g |

This cream is applied to chestnut hair for 30 minutes. The hair is then rinsed, shampooed and dried. It then possesses a purple-violet sheen.

EXAMPLE 8

The following composition is prepared:

| | |
|---|---|
| 2,5-Dihydroxy-3-methyl-6-methoxy-1,4-benzoquinone | 0.1 g |
| N—(2'-chloro-4'-hydroxyphenyl)-3-acetylamino-6-methoxy-1,4-benzoquinone-imine | 0.03 g |
| Vinyl acetate/crotonic acid copolymer (90/10) | 1.8 g |
| Vinylpyrrolidone/vinyl acetate copolymer (60/40) | 0.4 g |
| 96° strength ethyl alcohol q.s. | 50° alcoholic strength |
| Citric acid q.s. | pH 3.5 |
| Distilled water q.s. | 100 g |

This setting lotion is applied to light blond hair. After drying and shaping, the hair possesses a pearlescent sheen.

EXAMPLE 9

The following composition is prepared:

| | |
|---|---|
| 2,5-Dihydroxy-3-methyl-6-methoxy-1,4-benzoquinone | 0.15 g |
| 2,6-Dimethyl-1,4-benzoquinone | 0.1 g |
| SACTIPON 8533 | 25 g |
| 2-Ethoxyethanol | 15 g |
| Citric acid q.s. | pH 2.5 |
| Distilled water q.s. | 100 g |

This composition is a colouring shampoo which is applied to yellowing grey hair. After a period of 20 minutes, rinsing and drying, the yellow has been removed from the hair perfectly.

EXAMPLE 10

The following composition is prepared:

| | |
|---|---|
| 2,3,5,6-Tetrahydroxy-1,4-benzoquinone dihydrate | 1 g |
| 2-Methoxy-1,4-benzoquinone | 1 g |
| Powdered extraction residue of saponaria | 35 g |
| Powdered maize cobs | 15 g |
| Citric acid | 4 g |
| Vidogum L 175 sold by UNIPECTINE | 3 g |
| Skimmed milk powder q.s. | 100 g |

This powder is diluted with 3 times its weight of warm water. The poultice thus obtained is applied to light chestnut hair for 20 minutes. After rinsing, shampooing and drying, the hair has a coppery golden sheen.

The tradenames denote the following products:

| | |
|---|---|
| MERGITAL CS 15 E | Cetyl/stearyl alcohol containing 15 mols of ethylene oxide, sold by HENKEL. |
| SACTIPON 8533 | Sodium salt of sulphated oxyethyleneated alkanol containing 0.6 milliequivalents/g, sold by LEVER. |

We claim:

1. A process for dyeing human hair, which comprises the steps of applying to said hair a composition which comprises, in a cosmetically acceptable medium, an amount of about 0.05 to 3% by weight of a benzoquinone derivative of the formula:

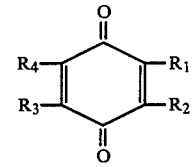

in which $R_1$ and $R_3$ independently denote a hydrogen atom, a hydroxyl group, an alkyl group, an alkoxy group, or a hydroxylated alkyl group, and $R_2$ and $R_4$ independently denote a hydrogen atom, a hydroxyl, alkoxy, alkyl or phenyl group, or an alkoxy, alkyl or phenyl group substituted by OH, such that at most two of $R_1$, $R_2$, and $R_3$, and $R_4$ denote alkyl or alkoxy groups; if one of the radicals $R_1$, $R_2$, $R_3$ or $R_4$ denote a methyl, hydroxyl or methoxy group, at least one of the others is other than hydrogen and if two of the radicals $R_1$, $R_2$, $R_4$ are identical and located in the para-position relative to one another, and denote methoxy or hydroxyl at least one of the other two is other than hydrogen, the alkyl and alkoxy groups having 1 to 3 carbon atoms, said composition being applied in an effective amount for dyeing said hair; leaving said composition on the hair for 5 to 60 minutes; and rinsing and drying said hair.

2. Process according to claim 1, wherein the composition is in a form selected from the group consisting of liquids, creams, gels, oils, and powders.

3. Process according to claim 1 in which the cosmetically acceptable medium is a solid medium selected from the group consisting of silicas, clays, plants powdered after solvent extraction of the active principle in said plants, a flour, a starchy substance and a mucilagenous substance, said composition being diluted with a liquid at the time of use to form a mixture having a viscosity from 300 to 5000 centipoises.

4. Process according to claim 1 in which the composition further comprises an amount of about 0.01 to 5% by weight of another dyestuff selected from the group consisting of anthraquinone dyes, azo dyes, nitro dyestuffs of the benzene series, indophenols, indamines, indoanilines, and hydroxylated benzaldehyde derivatives.

5. A process according to claim 1 wherein said benzoquinone derivative is in the form of a powder which is stable during storage; and wherein said composition further comprises a solid medium selected from the group consisting of silicas, clays, plants powdered after solvent extraction of the active principle in said plants, a flour, a starchy substance and a mucilagenous substance, said composition being diluted at the time of use with a liquid selected from the group consisting of water, an alcohol, a glycol, and an oil.

6. A composition suitable for dyeing human hair which comprises, in a cosmetically acceptable medium, an amount of about 0.1 to 5% by weight of a benzoquinone derivative selected from the group consisting of: 2,3,5,6-tetrahydroxy-1,4-benzoquinone, 2,hydroxy-3-methyl-6-methoxy-1,4-benzoquinone, 2,5-dihydroxy-3-methyl-6-methoxy-1,4-benzoquinone, 2,5-dihydroxy-3,6-dimethoxy-1,4-benzoquinone, 2-hydroxy-3-methyl-5,6-dimethoxy-1,4-benzoquinone, 2,5-dihydroxy-3-methyl-1,4-benzoquinone, 2-hydroxy-3-methoxy-5,6-dimethyl-1,4-benzoquinone, 2-hydroxy-6-methyl-1,4-benzoquinone, 2-hydroxy-3-methoxy-6-methyl-1,4-benzoquinone, 2,3-dihydroxy-5-methyl-1,4-benzoquinone, 2,3-dihydroxy-5,6-dimethyl-1,4-benzoquinone, 2,6-dimethyl-1,4-benzoquinone, 2-methyl-5-isopropyl-1,4-benzoquinone, 2,5-dihydroxy-3,6-diphenyl-1,4-benzoquinone and 2,5-dihydroxy-3,6-di-(4'-hydroxyphenyl)-1,4-benzoquinone.

7. A composition according to claim 6, which further comprises an amount of about 0.01 to 5% by weight of another direct dyestuff in addition to the benzoquinone derivative of formula (I), said another direct dyestuff being selected from the group consisting of anthraquinone dyestuffs, azo dyestuffs, nitro dyestuffs of the benzene series, indophenols, indamines, indoanilines and hydroxylated benzaldehyde derivatives.

8. A composition according to claim 6, wherein said cosmetically acceptable medium is a solid medium selected from the group consisting of a powder, a flour, a starchy substance and a mucilagenous substance, said composition being diluted with a liquid at the time of use to form a mixture having a viscosity from 300 to 5000 centipoises, said liquid being selected from the group consisting of water, an alcohol, glycol, and an oil.

9. A composition according to claim 8, wherein said powder is selected from the group consisting of silicas, clays, and plants powdered after solvent extraction.

10. A composition suitable for dyeing human hair which comprises, in an aqueous medium, an amount of about 0.05 to 3% by weight of a benzoquinone derivative selected from the group consisting of: 2,3,5,6-tetrahydroxy-1,4-benzoquinone, 2,hydroxy-3-methyl-6-methoxy-1,4-benzoquinone, 2,5-dihydroxy-3-methyl-6-methoxy-1,4-benzoquinone, 2,5-dihydroxy-3,6-dimethoxy-1,4-benzoquinone, 2-hydroxy-3-methyl-5,6-dimethoxy-1,4-benzoquinone, 2,5-dihydroxy-3-methyl-1,4-benzoquinone, 2-hydroxy-3-methoxy-5,6-dimethyl-1,4-benzoquinone, 2-hydroxy-6-methyl-1,4-benzoquinone, 2-hydroxy-3-methoxy-6-methyl-1,4-benzoquinone, 2,3-dihydroxy-5-methyl-1,4-benzoquinone, 2,3-dihydroxy-5,6-dimethyl-1,4-benzoquinone, 2,6-dimethyl-1,4-benzoquinone, 2-methyl-5-isopropyl-1,4-benzoquinone, 2,5-dihydroxy-3,6-diphenyl-1,4-benzoquinone and 2,5-dihydroxy-3,6-di-(4'-hydroxyphenyl)-1,4-benzoquinone.

11. A composition according to claim 10 which further comprises an adjuvant selected from the group consisting of anionic, cationic, non-ionic or amphoteric surface-active agents, solvents, polymers, thickeners, penetrating agents, sequestering agents, buffers, perfumes, and antioxidants.

12. A process for dyeing human hair, which comprises the steps of applying to said hair a composition which comprises, in an aqueous medium, an amount of about 0.05 to 3% by weight of a benzoquinone derivative of the formula:

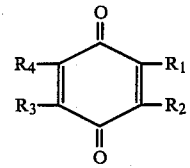

in which $R_1$ and $R_3$ independently denote a hydrogen atom, a hydroxyl group, an alkyl group, an alkoxy group, or a hydroxylated alkyl group, and $R_2$ and $R_4$ independently denote a hydrogen atom, a hydroxyl, alkoxy, alkyl or phenyl group, or an alkoxy, alkyl or phenyl group substituted by OH, such that at most two of $R_1$, $R_2$, $R_3$, and $R_4$ denote alkyl or alkoxy groups; if one of the radicals $R_1$, $R_2$, $R_3$ or $R_4$ denote a methyl, hydroxyl or methoxy group, at least one of the others is other than hydrogen and if two of the radicals $R_1$, $R_2$, $R_3$ or $R_4$ are identical and located in the para-position relative to one another, and denote methoxy or hydroxyl at least one of the other two is other than hydrogen, the alkyl and alkoxy groups having 1 to 3 carbon atoms, said composition being applied in an effective amount for dyeing said hair; leaving said composition on the hair for 5 to 60 minutes; and rinsing and drying said hair.

13. A process for dyeing human hair which comprises the steps of applying to said hair a composition which comprises an aqueous medium and an amount of about 0.5 to 3% by weight of a benzoquinone derivative; leaving said composition on the hair for 5 to 60 minutes; and rinsing and drying said hair, said composition being applied in an effective amount for dyeing said hair and said benzoquinone derivative being selected from the group consisting of:

2,3,5,6-tetrahydroxy-1,4-benzoquinone, 2,hydroxy-3-methyl-6-methoxy-1,4-benzoquinone, 2,5-dihydroxy-3-methyl-6-methoxy-1,4-benzoquinone, 2,5-dihydroxy-3,6-dimethoxy-1,4-benzoquinone, 2-hydroxy-3-methyl-5,6-dimethoxy-1,4-benzoquinone, 2,5-dihydroxy-3-methyl-1,4-benzoquinone, 2-hydroxy-3-methoxy-5,6-dimethyl-1,4-benzoquinone, 2-hydroxy-6-methyl-1,4-benzoquinone, 2-hydroxy-3-methoxy-6-methyl-1,4-benzoquinone, 2,3-dihydroxy-5-methyl-1,4-benzoquinone, 2,3-dihydroxy-5,6-dimethyl-1,4-benzoquinone, 2,6-dimethyl-1,4-benzoquinone, 2-methyl-5-isopropyl-1,4-benzoquinone, 2,5-dihydroxy-3,6-diphenyl-1,4-benzoquinone and 2,5-dihydroxy-3,6-di-(4'-hydroxyphenyl)-1,4-benzoquinone.

14. A process for dyeing human hair, which comprises the steps of applying to said hair a composition comprising an aqueous medium, an amount of about 0.5 to 3% by weight of benzoquinone derivative, and an adjuvant selected from the group consisting of anionic, cationic, non-ionic, or amphoteric surface-active agents, solvents, polymers, thickeners, penetrating agents, sequestering agents, buffers, perfumes, and antioxidants; leaving said composition on the hair for 5 to 60 minutes; and rinsing and drying said hair, said composition being applied in an effective amount for dyeing said hair, and said benzoquinone derivative being selected from the group consisting of:

2,3,5,6-tetrahydroxy-1,4-benzoquinone, 2-hydroxy-3-methyl-6-methoxy-1,4-benzoquinone, 2,5-dihydroxy-3-methyl-6-methoxy-1,4-benzoquinone, 2,5-dihydroxy-3,6-dimethoxy-1,4-benzoquinone, 2-hydroxy-3-methyl-5,6-dimethoxy-1,4-benzoquinone, 2,5-dihydroxy-3-methyl-1,4-benzoquinone, 2-hydroxy-3-methoxy-5,6-dimethyl-1,4-benzoquinone, 2-hydroxy-6-methyl-1,4-benzoquinone, 2-hydroxy-3-methoxy-6-methyl-1,4-benzoquinone, 2,3-dihydroxy-5-methyl-1,4-benzoquinone, 2,3-dihydroxy-5,6-dimethyl-1,4-benzoquinone, 2,6-dimethyl-1,4-benzoquinone, 2-methyl-5-isopropyl-1,4-benzoquinone, 2,5-dihydroxy-3,6-diphenyl-1,4-benzoquinone and 2,5-dihydroxy-3,6-di-(4'-hydroxyphenyl)-1,4-benzoquinone.

* * * * *